US010596153B2

(12) United States Patent
Alam

(10) Patent No.: US 10,596,153 B2
(45) Date of Patent: Mar. 24, 2020

(54) ANTIMICROBIAL AGENTS AND THE METHOD OF SYNTHESIZING THE ANTIMICROBIAL AGENTS

(71) Applicant: Arkansas State University—Jonesboro, State University, AR (US)

(72) Inventor: Mohammad Abrar Alam, Jonesboro, AR (US)

(73) Assignee: Arkansas State University-Jonesboro, State University, AR (US)

( * ) Notice: Subject to any disclaimer, the term of this patent is extended or adjusted under 35 U.S.C. 154(b) by 0 days.

(21) Appl. No.: 15/607,108

(22) Filed: May 26, 2017

(65) Prior Publication Data

US 2017/0340609 A1    Nov. 30, 2017

Related U.S. Application Data

(60) Provisional application No. 62/342,811, filed on May 27, 2016.

(51) Int. Cl.
| A61K 31/415 | (2006.01) |
| C07D 513/22 | (2006.01) |
| C07D 231/56 | (2006.01) |
| A61K 31/69 | (2006.01) |

(52) U.S. Cl.
CPC .......... *A61K 31/415* (2013.01); *A61K 31/69* (2013.01); *C07D 231/56* (2013.01); *C07D 513/22* (2013.01)

(58) Field of Classification Search
None
See application file for complete search history.

(56) References Cited

U.S. PATENT DOCUMENTS 8,642,660 B2 *  2/2014  Goldfarb .............. A61K 31/122
                                                              514/641
9,867,879 B2 *  1/2018  Skaar ................. A61K 41/0057

OTHER PUBLICATIONS

Ren et al (Asian Journal of Chemistry (2014), 26(24), 8309-8313 CAS Abstract Only.*
Bekhit et al, Pak. J. Pharm. Sci., vol. 27, No. 6, Nov. 2014, pp. 1767-1773.*
Bekhit et al, Arch. Pharm. Chem. Life Sci. 2012, 345, 147-154.*

* cited by examiner

*Primary Examiner* — Kamal A Saeed
(74) *Attorney, Agent, or Firm* — Schrantz Law Firm, PLLC; Stephen D. Schrantz

(57) ABSTRACT

New 1,3-dipenyl pyrazole derived azomethines and N-aryl amines have been synthesized. These anti-MRSA agents combat MRSA and other infections. These azomethine and N-arylamine derivatives of benzoic acid provide combat MRSA and other infections.

4 Claims, 9 Drawing Sheets

R = H, F, Cl, F, F, and alkyl substituted
R' = OH, OMe, OCH₂O, F, Cl, Br, and I
R" = F, Cl, Br, and CF₃

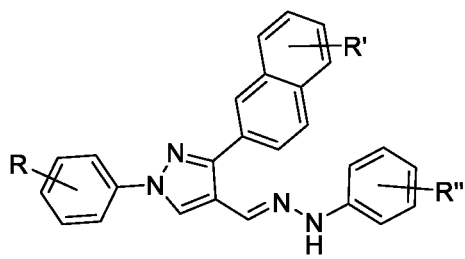

R = H, F, Cl, F, F, and alkyl substituted
R' = OH, OMe, OCH₂O, F, Cl, Br, and I
R" = F, Cl, Br, and CF₃

R = H, F, Cl, F, F, and alkyl substituted
R' = OH, OMe, OCH₂O, F, Cl, Br, and I
R" = F, Cl, Br, and CF₃

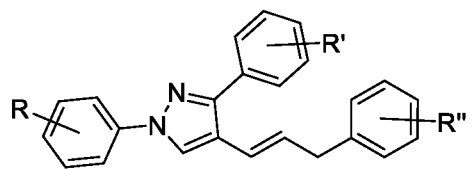

R = H, F, Cl, F, F, and alkyl substituted
R' = OH, OMe, OCH₂O, F, Cl, Br, and I
R" = F, Cl, Br, and CF₃

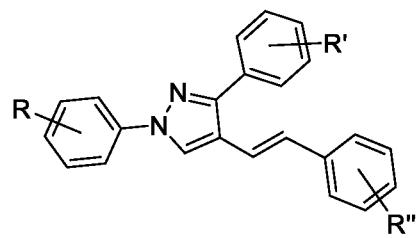

R = H, F, Cl, F, F, and alkyl substituted
R' = OH, OMe, OCH₂O, F, Cl, Br, and I
R" = F, Cl, Br, and CF₃

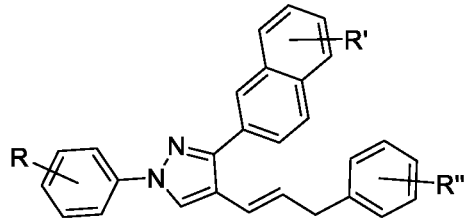

R = H, F, Cl, F, F, and alkyl substituted
R' = OH, OMe, OCH₂O, F, Cl, Br, and I
R" = F, Cl, Br, and CF₃

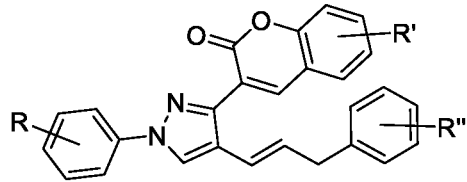

R = H, F, Cl, F, F, and alkyl substituted
R' = OH, OMe, OCH₂O, F, Cl, Br, and I
R" = F, Cl, Br, and CF₃

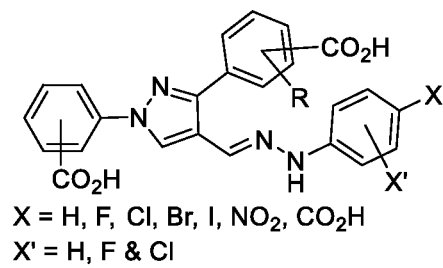

X = H, F, Cl, Br, I, NO₂, CO₂H
X' = H, F & Cl

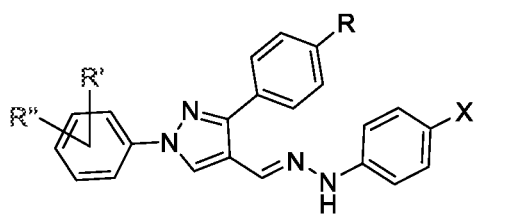

R = OH & CO₂H; X = F, Cl, & Br
R' = H, F, Cl, Br, I, NO₂, CH₃, Et, iPr, OMe, OH, CF₃, CN, SO₃H, & CO₂H
R" = H, F, Cl, CH₃,

FIG. 3A

R = H, CF₃, F, Cl, Br, NO₂, CN, CO₂H, & OMe (R = H, CH₃, & ⁱPr)

R' = F, Cl, Br, CF₃, CH₃, & CO₂H

ANTIMICROBIAL AGENTS AND THE METHOD OF SYNTHESIZING THE ANTIMICROBIAL AGENTS

CROSS-REFERENCE TO RELATED APPLICATIONS

This application claims priority to and is a continuation in part of U.S. Patent Application No. 62/342,811 filed on May 27, 2016 entitled "ANTIMICROBIAL AGENTS AND THE METHOD OF SYNTHESIZING THE ANTIMICROBIAL AGENTS".

STATEMENT REGARDING FEDERALLY SPONSORED RESEARCH OR DEVELOPMENT

Grant Number P30 GM103450 from the National Institute of General Medical Sciences of the National Institutes of Health (NIH) for recording mass spectrometry.

REFERENCE TO A MICROFICHE APPENDIX

Not Applicable.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND OF THE INVENTION

The present invention relates generally to synthesizing antimicrobial agents, including anti-Methicillin-resistant *Staphylococcus aureus* (MRSA) agents and anti-*acinetobacter* agents. Antimicrobial resistance to antibiotics is a global concern. Without urgent and coordinated action, the world is moving toward a post-antibiotic era, in which normal infections or minor injuries may become fatal. To combat this resistance, new 1,3-diphenyl pyrazole derivatives have been synthesized. Several compounds have shown growth inhibition up to 24 mm in size against *Staphylococcus aureus* inhibition studies. Testing the active compounds against Methicillin-resistant *Staphylococcus aureus* (MRSA) in minimum inhibitory concentration (MIC) tests showed activity as low as 16 µg/mL.

Antibiotic resistance to infection has become a worldwide problem in recent years. According to the latest Center for Disease Control (CDC) report more than two million people are infected every year with antibiotic-resistant infections and at least 23,000 are dying as a result of these diseases in the US alone. Methicillin-resistant *Staphylococcus aureus* (MRSA) has been prioritized by CDC as one of the serious threat bacteria.[1] MRSA infection in the community and in hospitals is estimated to be 64% more likely to kill a person than infection by a non-resistant strain.[2] In addition to mortality, MRSA infections result in an estimated $3 billion to $4 billion in healthcare cost per year.[3] One in three (33%) people carry *Staphylococcus* in their nose, usually without any health concern but 2% people carry MSRA that could be a serious threat to health. MSRA is resistant to several antibiotics and it is the most common pathogen to cause skin and soft tissue infections.[4] In the general community, MSRA causes skin infection at high probability and other minor infections but in a healthcare setting it can cause systemic infection, pneumonia, and surgical site infections. MRSA is an important public health problem and more needs to be done to decrease the risk of this infection. One of the four guidelines recommended by CDC to combat antibiotic resistance is promoting the development of new antibiotics and developing new diagnostic tests for resistant bacteria.[5]

DESCRIPTION OF THE KNOWN ART

Currently, many pyrazole derivatives have been approved as analgesic, anti-inflammatory, antimicrobial, anticonvulsant, antidepressant, antimycobacterial,[7] antiviral, and anti-tumor drugs. However, these derivatives are not potent antimicrobial agents.

The known art does not properly treat the antibiotic-resistant infections. Therefore, a need exists to treat such infections. The present invention provides these potent antimicrobial agents.

SUMMARY OF THE INVENTION

The present invention provides anti-microbial agents including anti-MRSA agents and anti-*acinetobacter* agents. The present invention also provides for a method of synthesizing the antimicrobial agents, including anti-MRSA agents and anti-*acinetobacter* agents. Antimicrobial resistance to antibiotics is a global concern. Without urgent and coordinated action, the world is moving toward a post-antibiotic era, in which normal infections or minor injuries may become fatal. To combat this resistance, the present invention provides for antimicrobial agents and the synthesis of 1,3-diphenyl pyrazole derivatives. Several compounds have shown growth inhibition up to 24 mm in size against *Staphylococcus aureus* inhibition studies. These active compounds against Methicillin-resistant *Staphylococcus aureus* (MRSA) in minimum inhibitory concentration (MIC) tests and found activity as low as 16 µg/mL.

It is an object of the present invention to provide an antimicrobial agent.

It is another object of the present invention to synthesize an antimicrobial agent.

It is another object of the present invention to combat antibiotic resistant infections.

It is another object of the present invention to provide an azomethine and N-arylamine derivatives of benzoic acid as an antimicrobial agent.

It is another object of the present invention to provide new 1,3-dipenyl pyrazole derived azomethines and N-aryl amines.

It is another object of the present invention to synthesize new 1,3-dipenyl pyrazole derived azomethines and N-aryl amines.

These and other objects and advantages of the present invention, along with features of novelty appurtenant thereto, will appear or become apparent by reviewing the following detailed description of the invention.

BRIEF DESCRIPTION OF THE DRAWINGS

In the following drawings, which form a part of the specification and which are to be construed in conjunction therewith, and in which like reference numerals have been employed throughout wherever possible to indicate like parts in the various views:

FIGS. 3A-3B are molecular views of one embodiment of the present invention;

DETAILED DESCRIPTION

Figure 1:
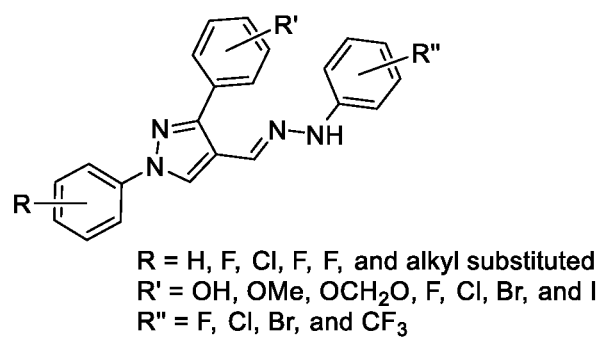
FIG. 1 is a molecular formula of one embodiment of the present invention.
Figure 2A:
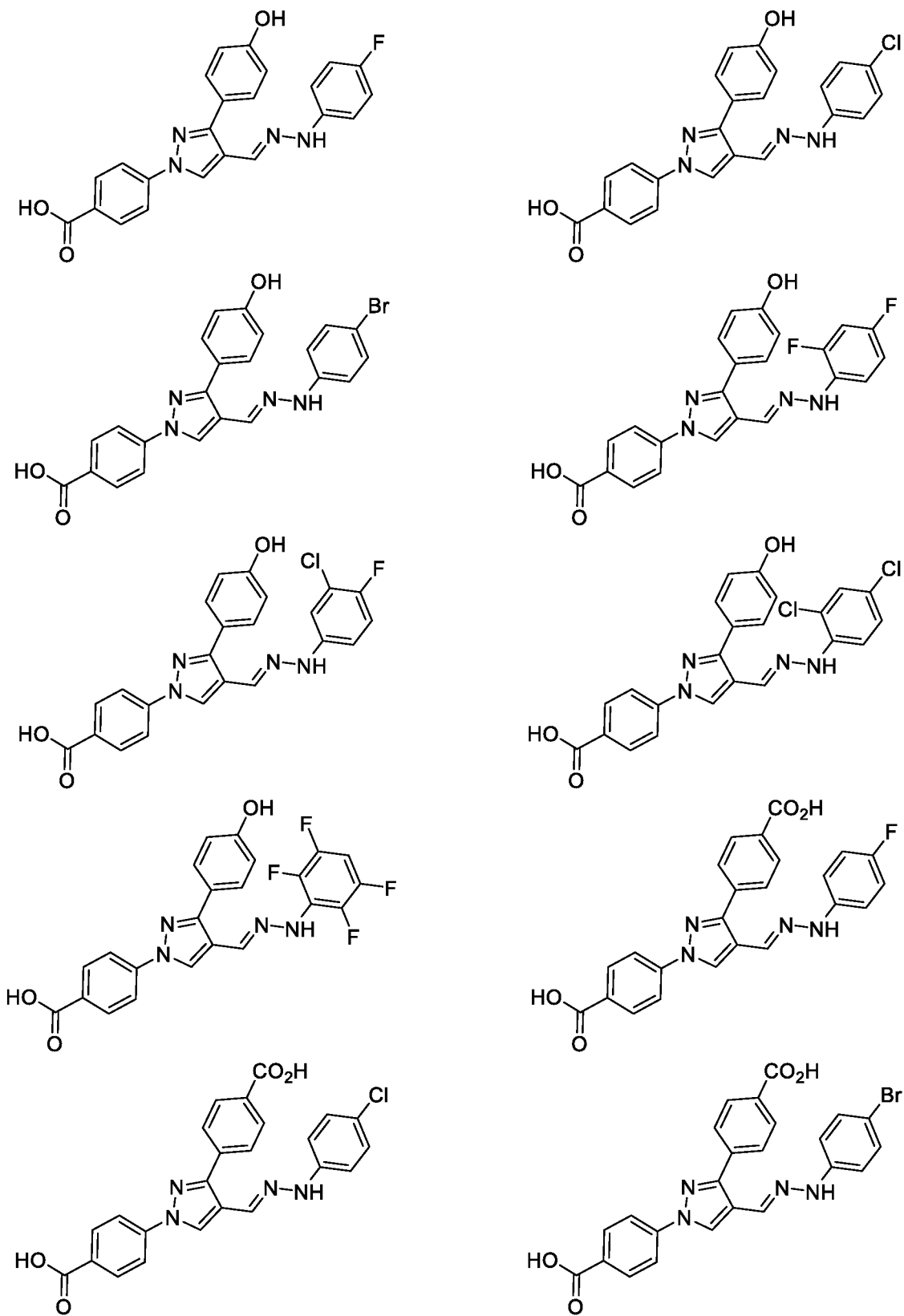
FIGS. 2A-2D are molecular views of one embodiment of the present invention.
Figure 2B:
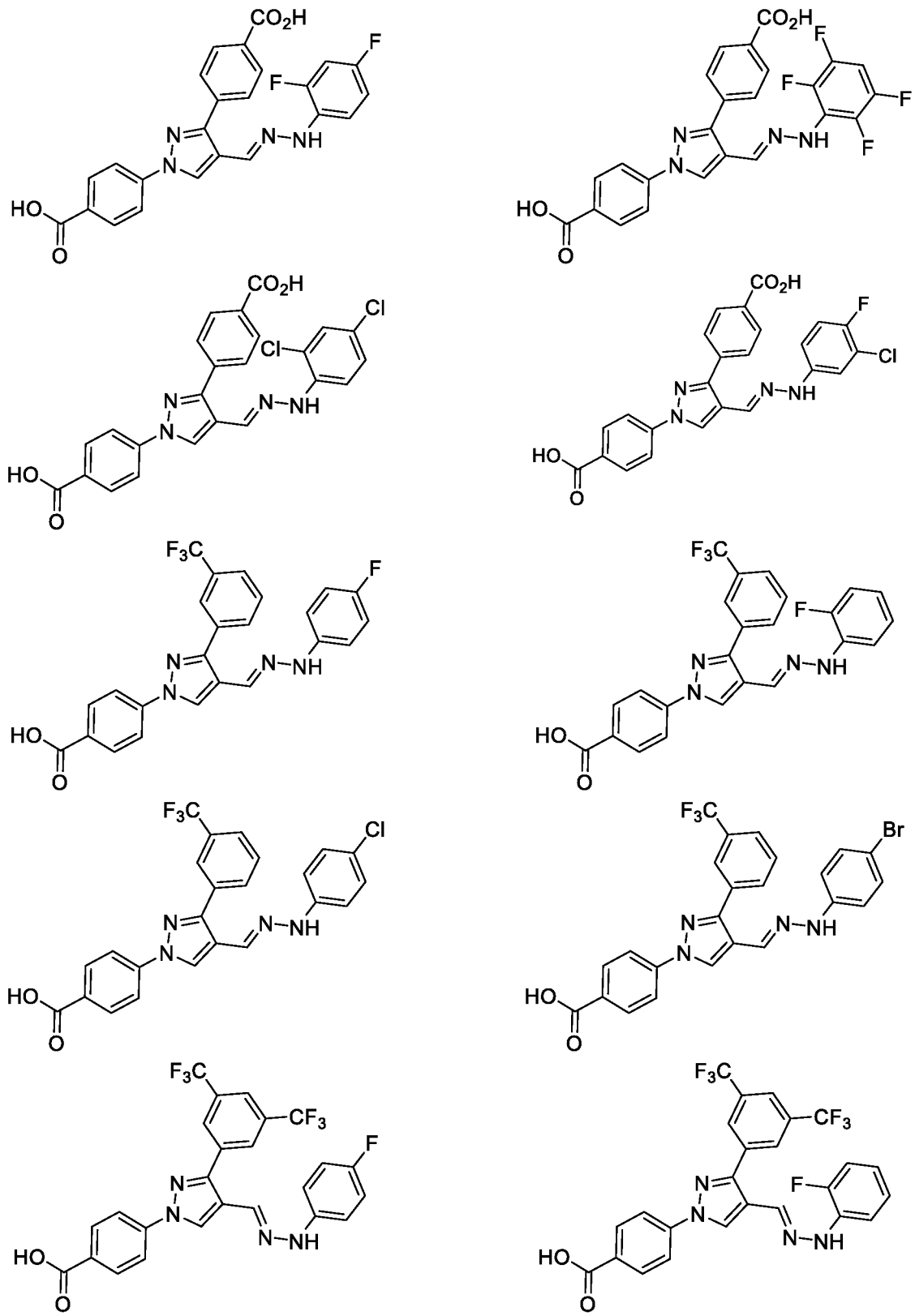
Figure 2C:
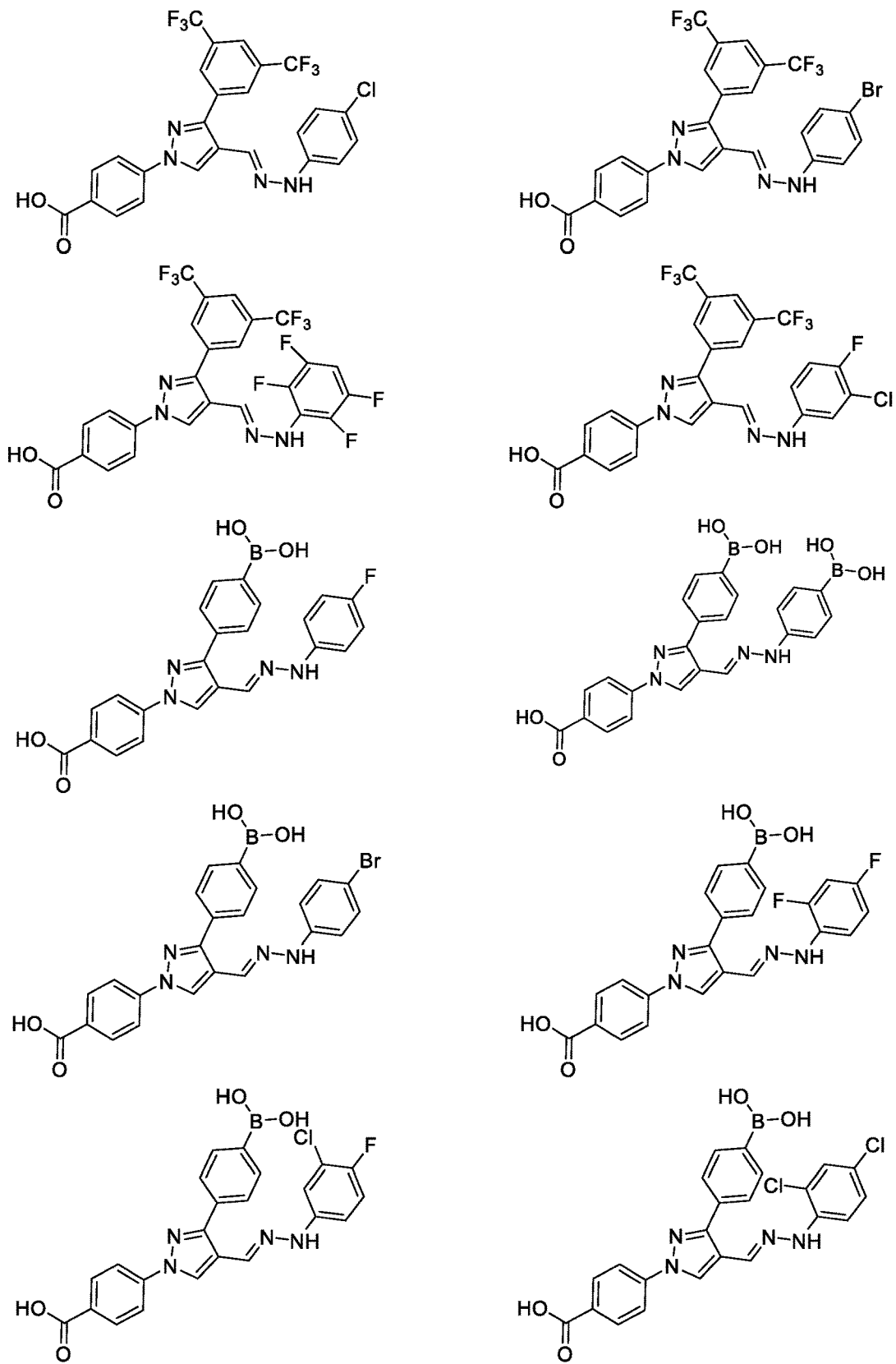
Figure 2D:
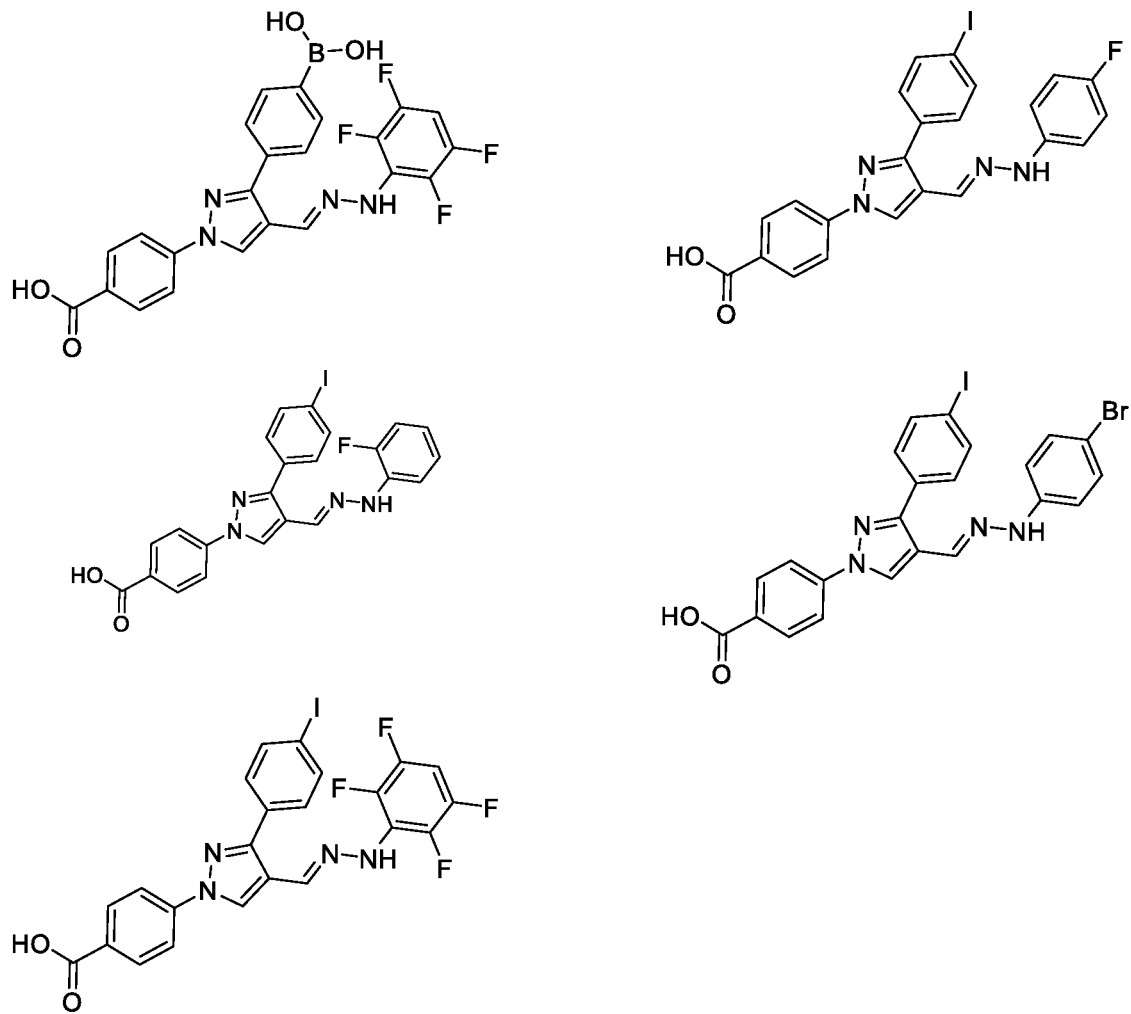

Antimicrobial agents of the present invention combat the antimicrobial resistance to antibiotics. The present invention relates to 1,3-diphenyl pyrazole derivatives and the synthesis of such derivatives to combat this resistance. Several compounds have shown growth inhibition up to 24 mm in size against *Staphylococcus aureus* inhibition studies. When the active compounds of the present invention are tested against Methicillin-resistant *Staphylococcus aureus* (MRSA) in minimum inhibitory concentration (MIC) tests, the results show activity as low as 16 µg/mL.

Pyrazoles (1,2-diazole) such as N-phenylpyrazoles and its phenyl analogues, ortho-terphenyl like motifs, are the privileged scaffolds. These moieties are found in a great number of drugs and drug candidates including best selling drugs.[6] Many pyrazole derivatives have been approved as analgesic, anti-inflammatory, antimicrobial, anticonvulsant, antidepressant, antimycobacterial,[7] antiviral, and antitumor drugs.[8] To get potent antimicrobial agents, several pyrazole-derived terphenyl like derivatives have been synthesized to test against MRSA.

The synthesis of the versatile starting material (3) starts from hydrazinobenzoic acid according to the modified literature procedure (FIG. 3).[9] Reaction of p-hydrazinobenzoic acid (1) with acetophenone in acetic acid yields the hydrazone derivative (2) as solid precipitate, which on filtration gives the pure hydrazone product (2). Reaction of hydrazone with POCl$_3$ in N,N-dimethyl formamide (Vilsmeier-Haack reagent) gives the crude pyrazolyl benzoic acid derivative, which on recrystallization in acetonitrile gives the pure product (3) in more than 80% overall yield. The present invention optimizes the reaction conditions to make this compound at a multi-gram scale. This versatile starting material has two dynamic functional groups for further derivatization.

The synthesis of the pyrazolyl benzoic acid derived aldehyde is shown at reference[9]. Pyrazole derived imines (azomethines) show wide range of biological activities.[10] Several azomethine derivatives (4a-s) of 3 were synthesized to obtain anti-microbial agents. Reaction of the aldehyde derivative (3) with different amines in refluxing toluene afforded the imine derivatives (4a-t), which on recrystallization with acetonitrile afforded the pure products in excellent yield.

Gram-positive bacteria: *Staphylococcus aureus* (S a) and *Bacillus subtilis* (B s), Gram-negative bacteria: *Pseudomonas aeruginosa* (P a) and *Escherichia coli* (E c), NA=No activity.

The reduction of imines (4a-s) with sodium borohydride in methanol afforded N-aryl amines results in very good yield. All imines (4a-q) were reduced by sodium borohydride to corresponding N-aryl amines except 4r and 4s. The reduction followed by recrystallization of these crude azomethines yielded the pure 5i, 5k, 5o, and 5t in good yield.

Disk Diffusion assays for antimicrobial activity were performed following Clinical and Laboratory Standards Institute guidelines. Bacteria were streaked onto Tryptic Soy Agar plates and incubated overnight at 35° C. Bacteria were suspended in sterile saline to the turbidity of a 0.5 McFarland standard then swabbed onto Mueller Hinton Agar plates to create lawns. Test compounds were dissolved in DMSO at a concentration of 0.1 M, and 10 µL of each were pipetted onto 6 mm diameter glass fiber disks placed on the lawns. Plates were incubated for 20-24 hours at 35° C. after which zones of inhibition (diameters in mm) were measured for each test compound. Bacteria used in these studies were *Staphylococcus aureus* ATCC 25923, *Pseudomonas aeruginosa* ATCC 27853, *Enterobacter aerogenes* ATCC 13048, and *Bacillus subtilis* ATCC 6633.

Azomethine derivatives (4a-s) showed moderate activity (zone of inhibition 7 mm to 11 mm) against *Bacillus subtilis*; a Gram-positive bacterium. Three of these imines (4l, 4o, and 4s) also showed moderate activity against *Staphylococcus aureus*. Phenoxyphenyl derivative (4h) is not soluble enough in the growth medium for antimicrobial activity. Reduced products (5a-t), N-aryl amine derivatives, showed good activity against *Staphylococcus aureus* in zone of inhibition assay in addition to showing activity against *Bacillus subtilis*. None of the N-aryl amines (5a-t) showed activity against Gram-negative bacteria. Encouraged by the zone of inhibition data, the tested synthesized compounds were tested against MRSA.

Anti-MRSA studies according to the following procedure: Compound stocks were prepared at 10 mg/mL DMSO solution and stored at 4° C. An aliquot of each sample was serially diluted two-fold across the wells of a micro titre plate to give an 8-point dose response (320-2.5 µg/mL). 5 µL was plated in duplicate (n=2) into a 384-well nonbinding surface plate (NBS, corning 3640) for each strain assayed against. Once cells were added this gave a final compound concentration range of 32-0.25 µg/mL. Vancomycin were used as positive bacterial inhibitor standard.

The Minimum Inhibitory Concentration (MIC) of the tested compounds was determined by broth microdilution plate based method as per CLSI guidelines for antimicrobial susceptibility testing of aerobic bacteria.[11] In brief, bacteria were cultured in Cation-adjusted Muller Hinton broth (CAMHB) at 37° C. overnight. A sample of each culture was then diluted 40-fold in fresh broth and incubated at 37° C. for 1.5-3 h. The resultant mid-log phase cultures were diluted (CFU/mL measured by OD600), then 45 µL was added to each well of the compound containing plates, giving a cell density of 5×105 CFU/mL and a final compound concentration range of 32-0.25 µg/mL. All the plates were covered and incubated at 37° C. for 18 h without shaking. Inhibition of bacterial growth was determined using resazurin as a marker for cell viability.[12] Resazurin was added to each well, at 0.001% final concentration, and plates incubated at 37° C. for 2 h. Fluorescence intensity was measured, ex 560/10 nm, em 590/10 nm (F560/590), using a Tecan M1000 Pro monochromator plate reader. The percentage of growth inhibition was calculated for each well, using the negative control (media only) and positive control (bacteria without inhibitors) on the same plate as comparators. The MIC was determined as the lowest concentration where there was no visible bacterial growth.

Several compounds have shown good activity against MRSA. Based on preliminary data, meta-substituted compounds with electron withdrawing group are more potent than the para-substituted compounds.

In conclusion, new 1,3-dipenyl pyrazole derived azomethines and N-aryl amines have been efficiently synthesized. Some of these molecules possess good antimicrobial activities, including anti-MRSA agents. Many variables in the lead molecules and ease of synthesis enables the optimization of the activity and drugability of potential antimicrobial agents.

The pyrazole derivatives have shown activity against *Acinetobacter baumannii* up to 0.85 0.85 µM concentration. The general structure of one embodiment of the pyrazole derivative as an antimicrobial agent is shown below and in FIG. 1:

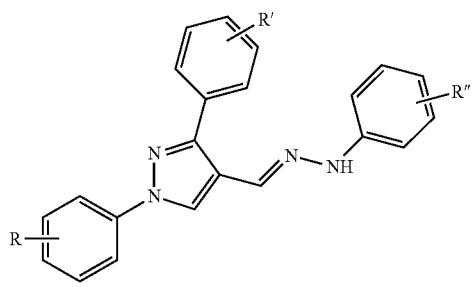

R = H, F, Cl, F, F, and alkyl sustituted
R′ = OH, OMe, OCH₂O, F, Cl, Br, and I
R″ = F, Cl, Br, and CF₃

The rings may be mono, di, tri, or polysubstituted. Such embodiments of the structure as shown in FIGS. 2A-2D may include, but are not limited to:

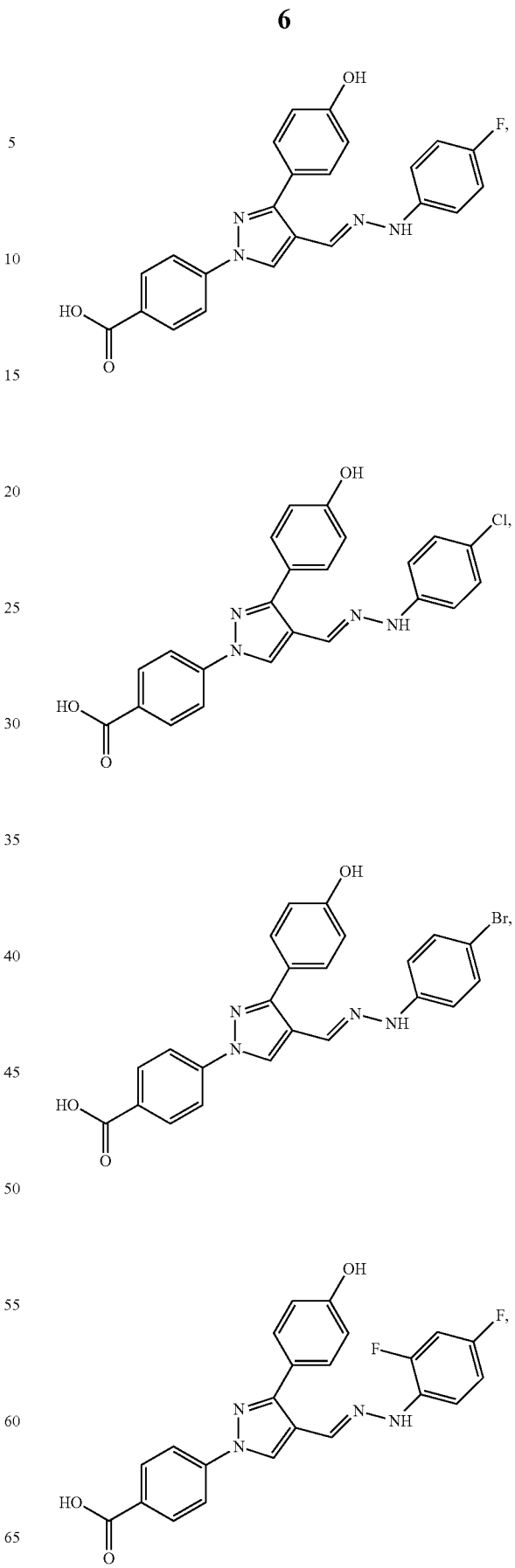

-continued
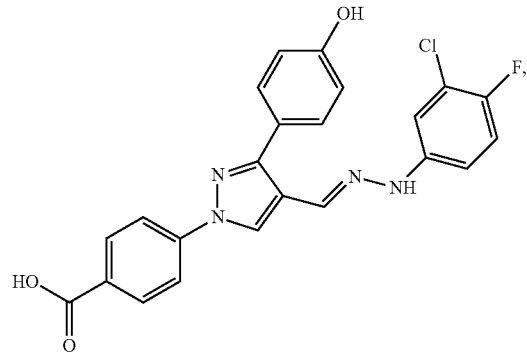
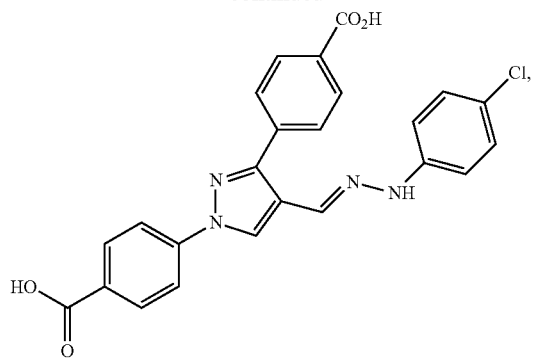
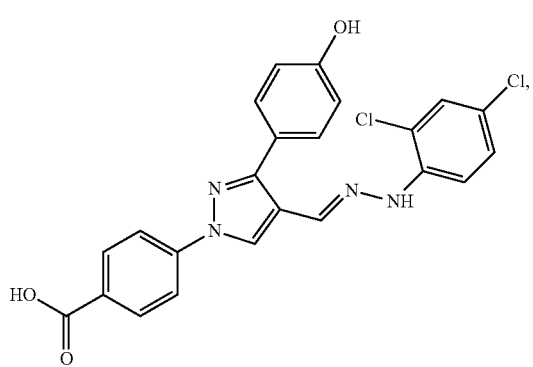
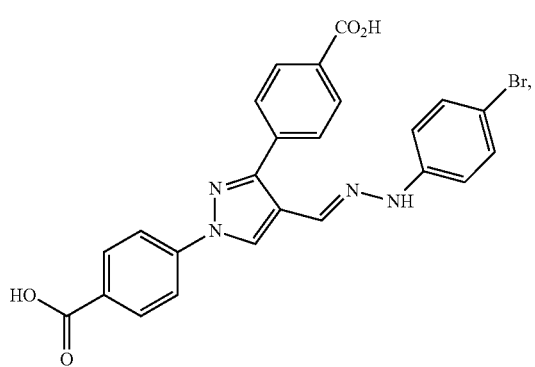
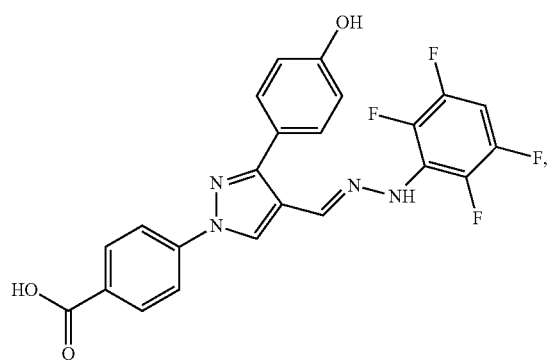
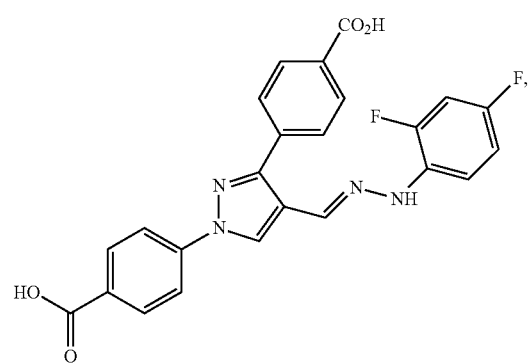
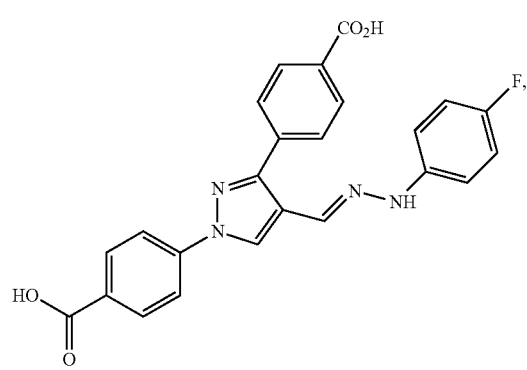
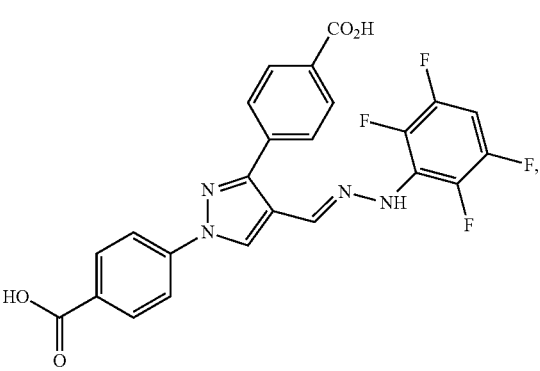

-continued

11
-continued
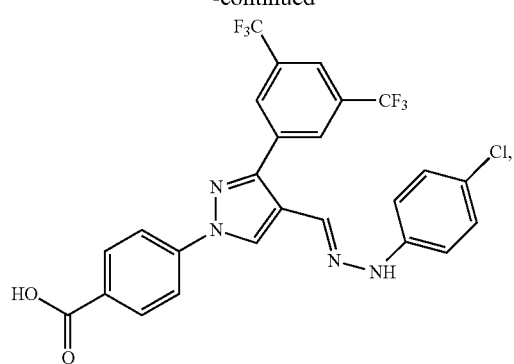
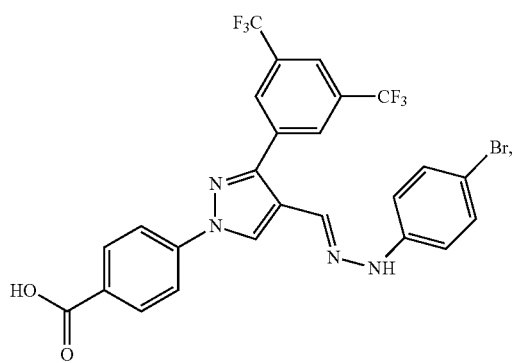
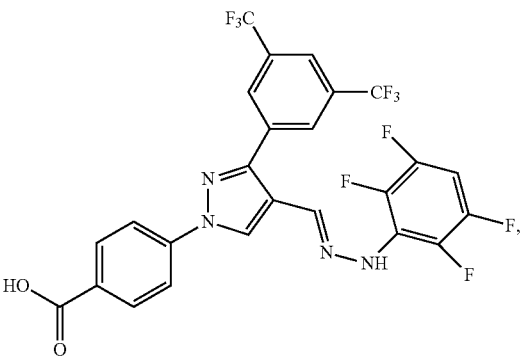
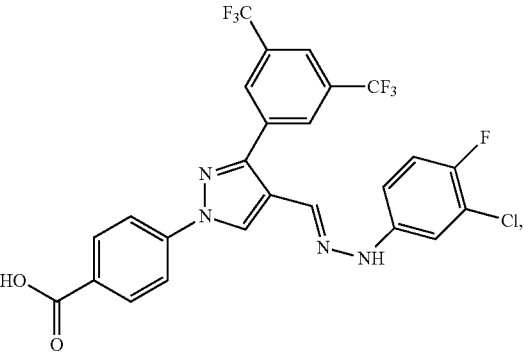
12
-continued
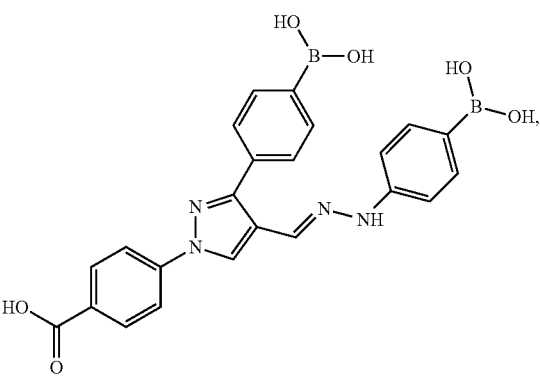
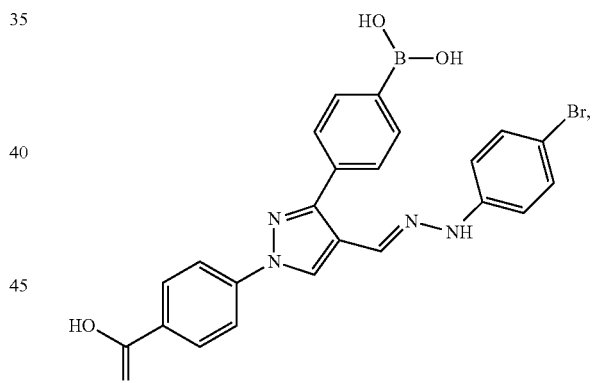
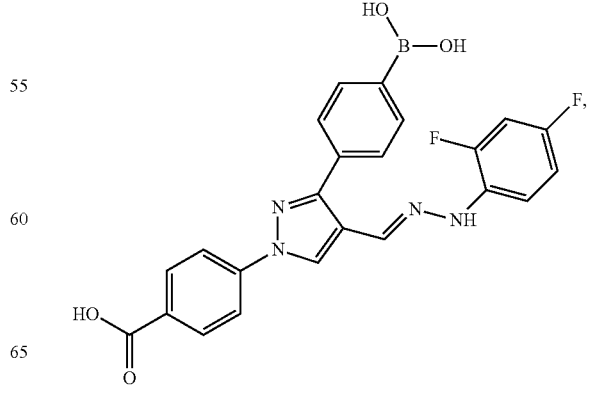

Figure 3B:
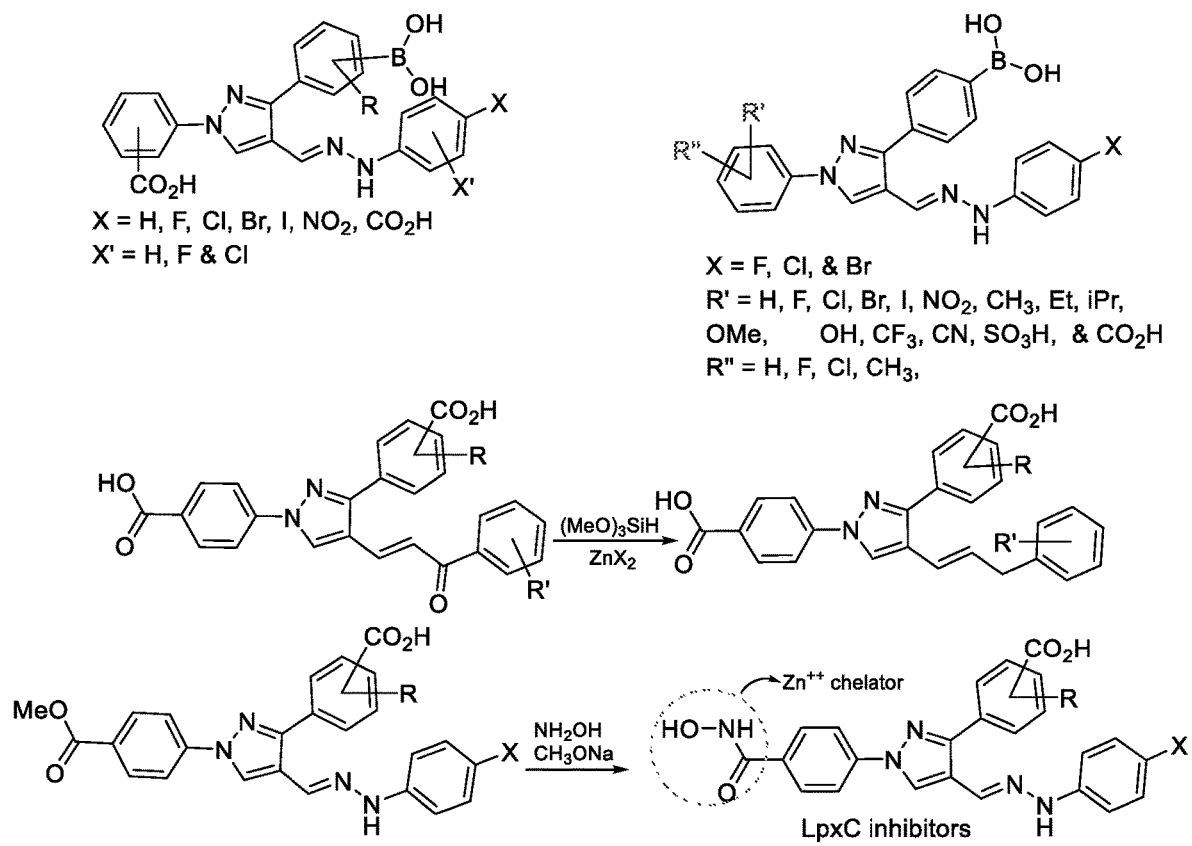
Figure 4:
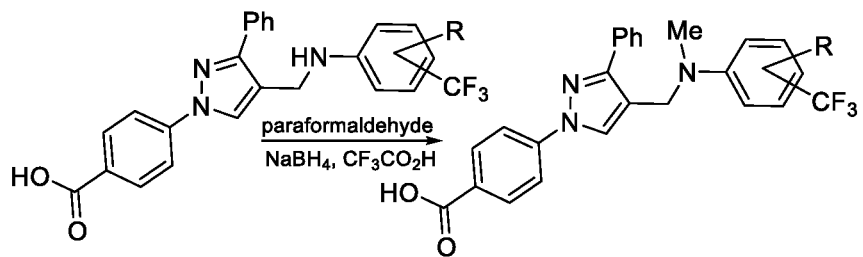
FIG. 4 is a molecular view of one embodiment of the present invention.
Figure 5:
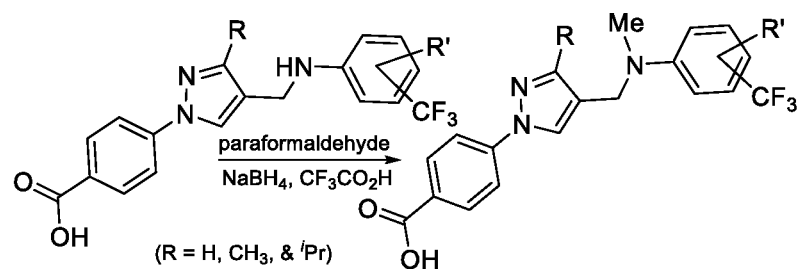
FIG. 5 is a molecular view of one embodiment of the present invention.
Figure 6:
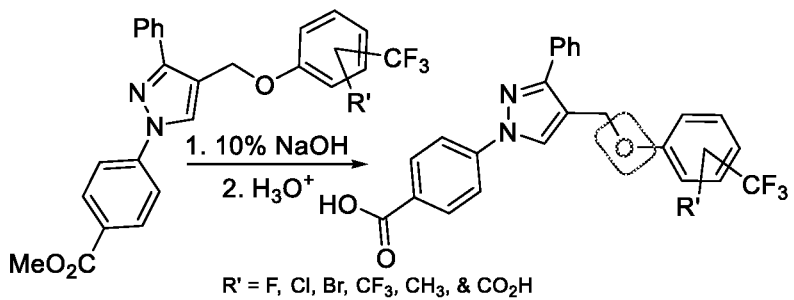
FIG. 6 is a molecular view of one embodiment of the present invention.
Figure 7:
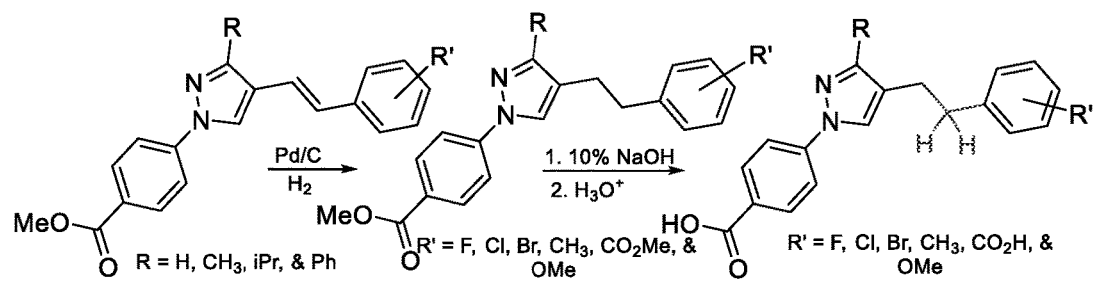
FIG. 7 is a molecular view of one embodiment of the present invention.
Figure 8:
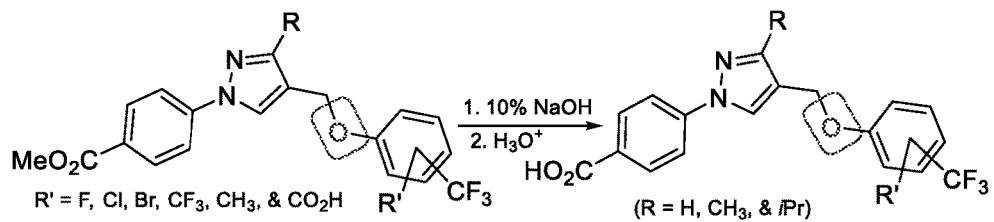
FIG. 8 is a molecular view of one embodiment of the present invention.
Figure 9:
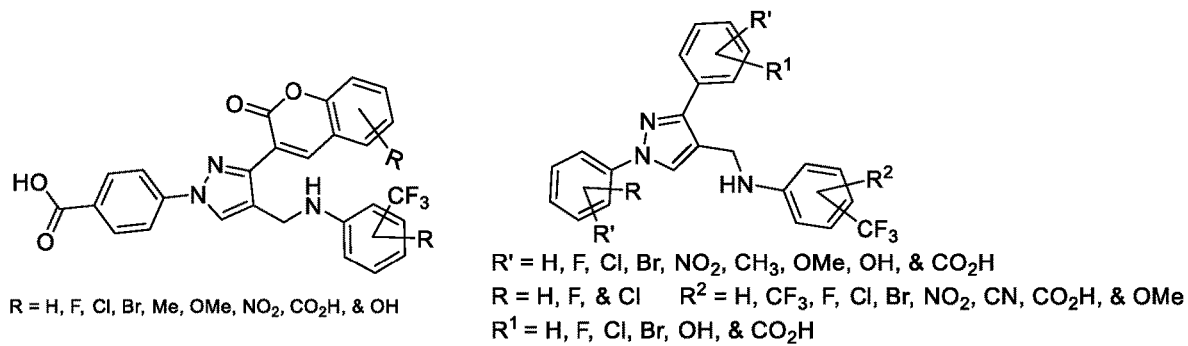
FIG. 9 is a molecular view of one embodiment of the present invention.

13
-continued
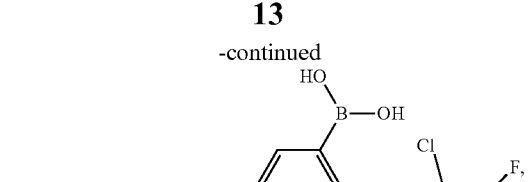
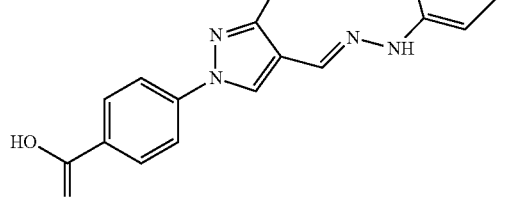
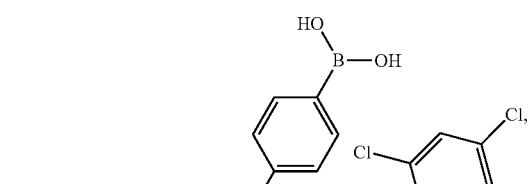
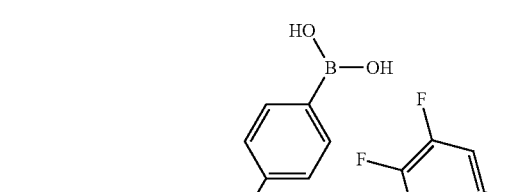
14
-continued
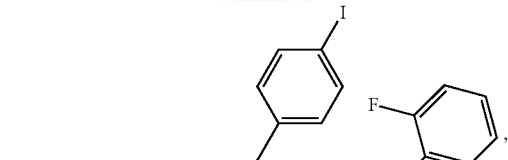
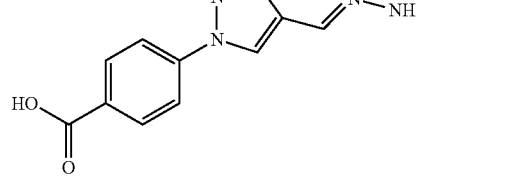
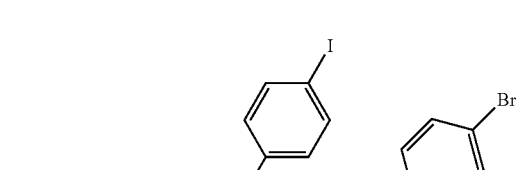
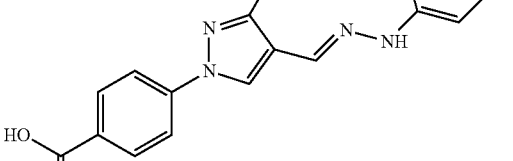
or a salt thereof.
Other variations of the structures as shown in FIGS. 3A-3B may include:
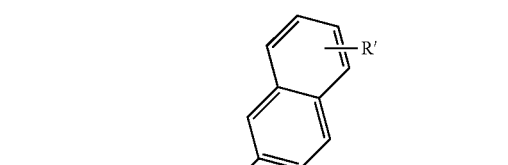
R = H, F, Cl, F, F, and alkyl substituted
R' = OH, OMe, OCH₂O, F, Cl, Br, and I
R'' = F, Cl, Br, and CF₃

15
-continued

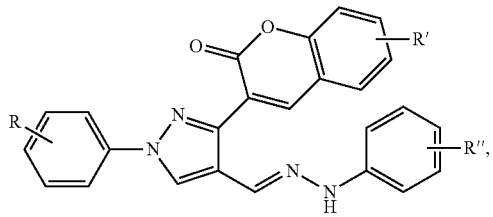

R = H, F, Cl, F, F, and alkyl substituted
R' = OH, OMe, OCH₂O, F, Cl, Br, and I
R'' = F, Cl, Br, and CF₃

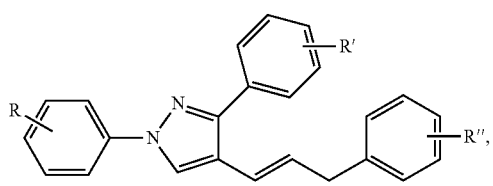

R = H, F, Cl, F, F, and alkyl substituted
R' = OH, OMe, OCH₂O, F, Cl, Br, and I
R'' = F, Cl, Br, and CF₃

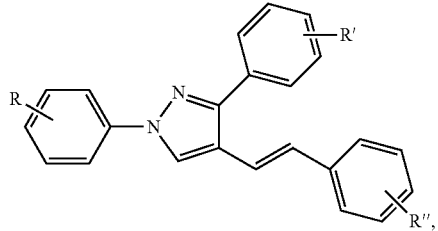

R = H, F, Cl, F, F, and alkyl substituted
R' = OH, OMe, OCH₂O, F, Cl, Br, and I
R'' = F, Cl, Br, and CF₃

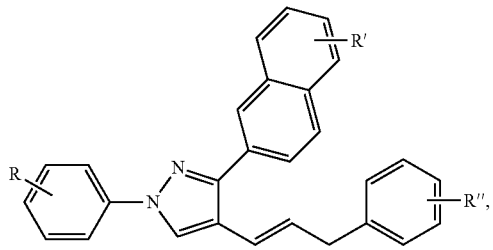

R = H, F, Cl, F, F, and alkyl substituted
R' = OH, OMe, OCH₂O, F, Cl, Br, and I
R'' = F, Cl, Br, and CF₃

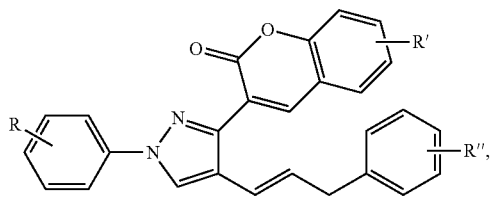

R = H, F, Cl, F, F, and alkyl substituted
R' = OH, OMe, OCH₂O, F, Cl, Br, and I
R'' = F, Cl, Br, and CF₃

16
-continued

X = H, F, Cl, Br, I, NO₂, CO₂H
X' = H, F, & Cl

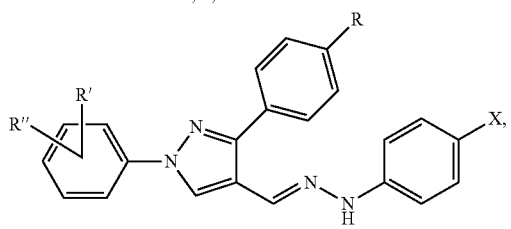

R = OH & CO₂H; X = F, Cl, & Br
R' = H, F, Cl, Br, I, NO₂, CH₃, Et, iPr, OMe, OH, CF₃, CN, SO₃H, & CO₂H
R'' = H, F, Cl, CH₃,

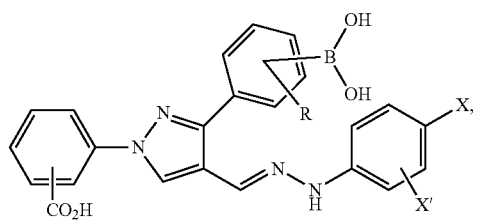

X = H, F, Cl, Br, I, NO₂, CO₂H
X' = H, F & Cl

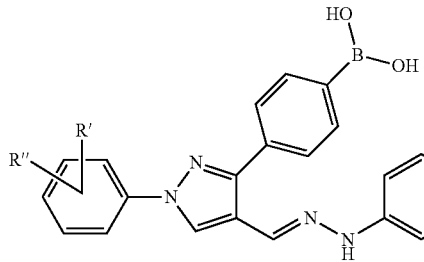

X = F, Cl, & Br
R' = H, F, Cl, Br, I, NO₂, CH₃, Et, iPr, OMe, OH, CF₃, CN, SO₃H, & CO₂H
R'' = H, F, Cl, CH₃, or a salt thereof.

The process of producing some examples of Anti-*Acinetebacter* agents as shown in FIG. 3B are shown below:

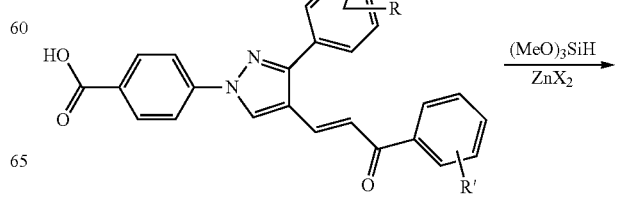

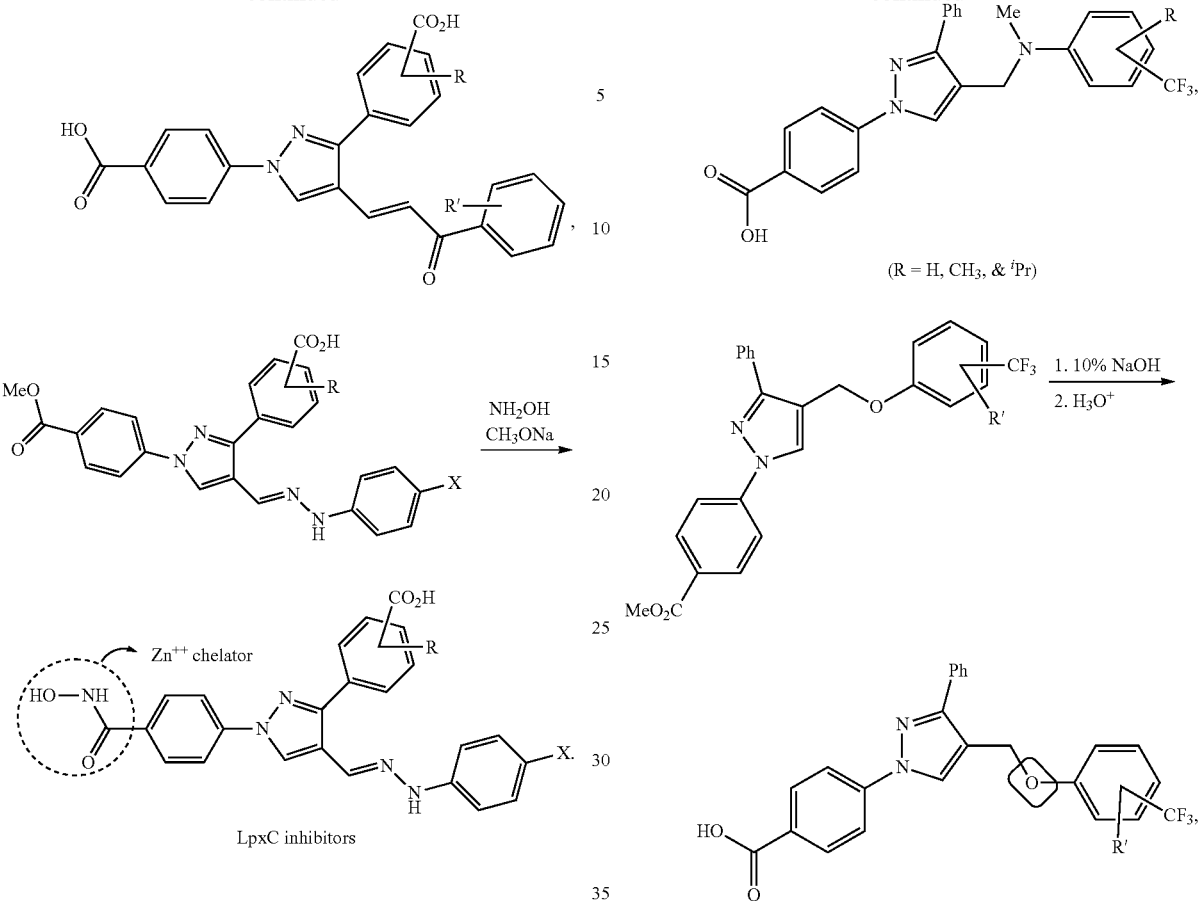
While the compounds provide anti-bacterial properties, the following compounds shown in FIGS. 4-9 provide anti-MRSA agents:
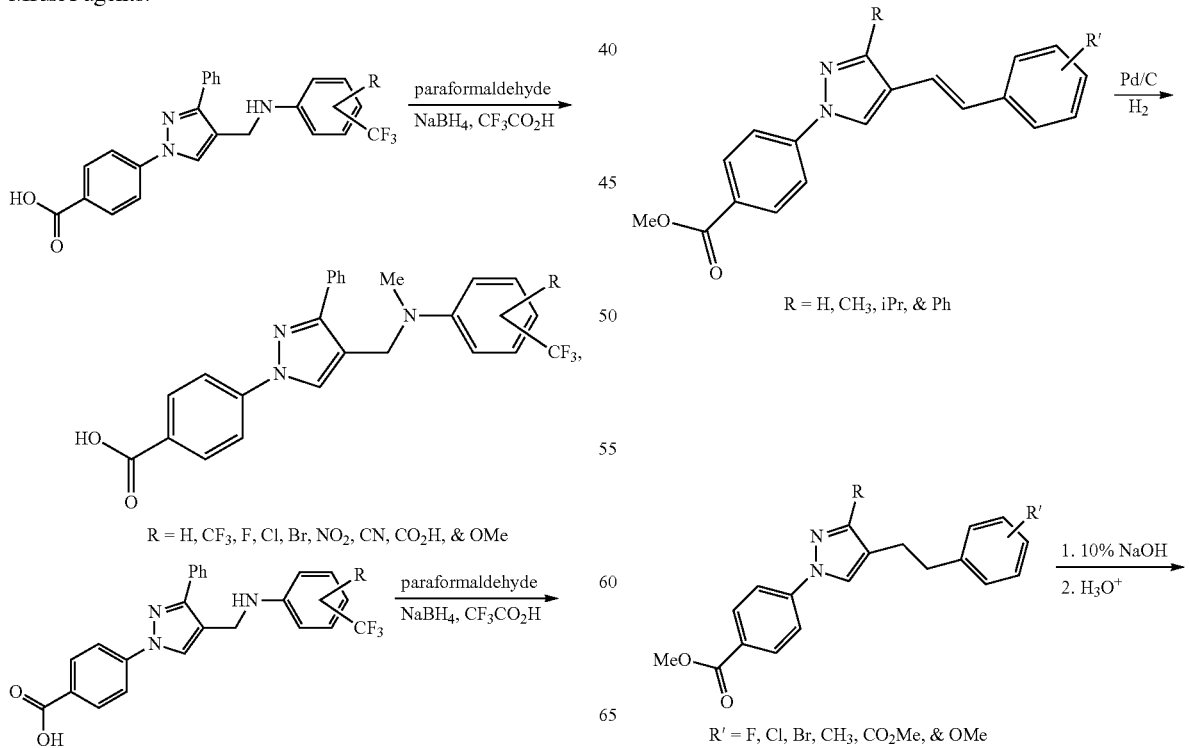

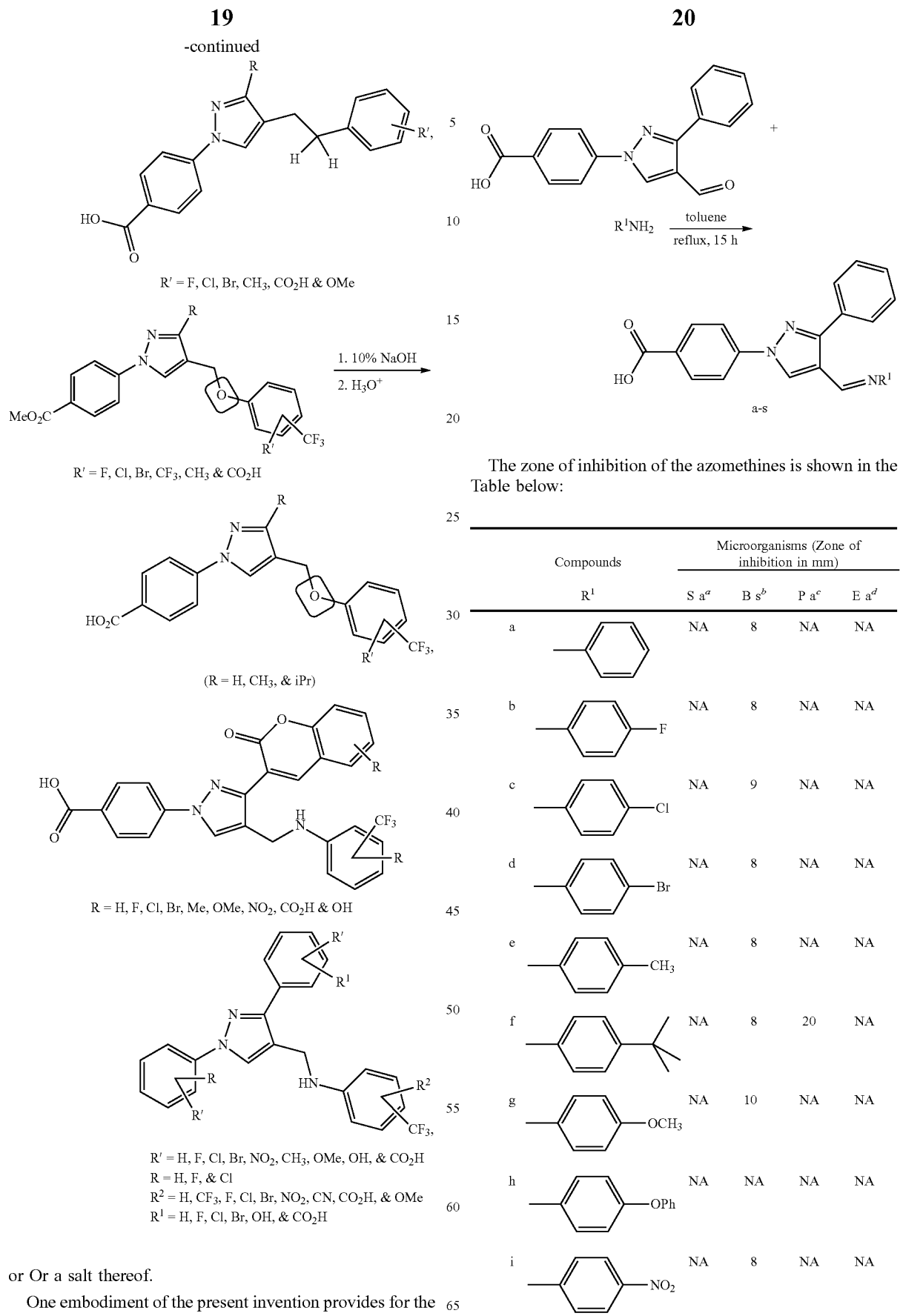

or Or a salt thereof.

One embodiment of the present invention provides for the synthesis of the imine derivatives, such as the azomethines. Such a scheme is shown below.

The zone of inhibition of the azomethines is shown in the Table below:

| Compounds | | Microorganisms (Zone of inhibition in mm) | | | |
|---|---|---|---|---|---|
| | $R^1$ | S $a^a$ | B $s^b$ | P $a^c$ | E $a^d$ |
| a | phenyl | NA | 8 | NA | NA |
| b | 4-F-phenyl | NA | 8 | NA | NA |
| c | 4-Cl-phenyl | NA | 9 | NA | NA |
| d | 4-Br-phenyl | NA | 8 | NA | NA |
| e | 4-CH$_3$-phenyl | NA | 8 | NA | NA |
| f | 4-tBu-phenyl | NA | 8 | 20 | NA |
| g | 4-OCH$_3$-phenyl | NA | 10 | NA | NA |
| h | 4-OPh-phenyl | NA | NA | NA | NA |
| i | 4-NO$_2$-phenyl | NA | 8 | NA | NA |

-continued

| Compounds | | Microorganisms (Zone of inhibition in mm) | | | |
|---|---|---|---|---|---|
| | $R^1$ | $S\,a^a$ | $B\,s^b$ | $P\,a^c$ | $E\,a^d$ |
| j | 3-F-C6H4 | NA | 8 | NA | NA |
| k | 3-Cl-C6H4 | NA | 7 | NA | NA |
| l | 3-Br-C6H4 | 9 | 9 | NA | NA |
| m | 3-OCF3-C6H4 | NA | 9 | NA | NA |
| n | 3-CF3-C6H4 | NA | 10 | NA | NA |
| o | 2-naphthyl | 13 | 8 | NA | NA |
| p | 3,4-methylenedioxyphenyl | NA | 8 | NA | NA |
| q | 3,4,5-tri-OCH3-C6H2 | NA | 7 | NA | NA |
| r | 3,4,5-tri-Br-C6H2 | NA | NA | NA | NA |
| s | 3,5-di-Cl-4-OH-C6H2 | 10 | 11 | NA | NA |

One embodiment of the present invention provides for the synthesis of the imine derivatives, such as the N-aryl amines. Such a scheme is shown below.

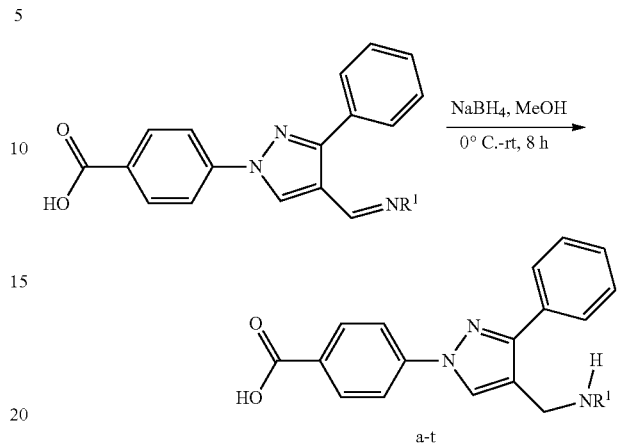

The zone of inhibition of the N-arylamine derivatives is shown in the Table below:

| Compounds | | Microorganisms (Zone of inhibition in mm) | | | |
|---|---|---|---|---|---|
| | $R^1$ | $S\,a^a$ | $B\,s^b$ | $P\,a^c$ | $E\,a^d$ |
| a | C6H5 | 20 | NA | NA | NA |
| b | 4-F-C6H4 | 18 | 18 | NA | NA |
| c | 4-Cl-C6H4 | 18 | 18 | NA | NA |
| d | 4-Br-C6H4 | 9 | 8 | NA | NA |
| e | 4-CH3-C6H4 | 17 | 18 | NA | NA |
| f | 4-tBu-C6H4 | 8 | 14 | NA | NA |
| g | 4-OCH3-C6H4 | 15 | 14 | NA | NA |
| h | 4-OPh-C6H4 | 11 | 12 | NA | NA |
| i | 4-CO2H-C6H4 | 11 | 10 | NA | NA |

-continued

| Compounds | | Microorganisms (Zone of inhibition in mm) | | | |
|---|---|---|---|---|---|
| | R[1] | S a[a] | B s[b] | P a[c] | E a[d] |
| j | 4-NO$_2$-phenyl | NA | 10 | NA | NA |
| k | 4-CF$_3$-phenyl | 10 | 9 | NA | NA |
| l | 3-F-phenyl | 20 | 18 | NA | NA |
| m | 3-Cl-phenyl | 11 | NA | NA | NA |
| n | 3-Br-phenyl | 11 | 18 | NA | NA |
| o | 3-NO$_2$-phenyl | 12 | 15 | NA | NA |
| p | 3-CF$_3$-phenyl | 19 | 24 | NA | NA |
| q | 3-OCF$_3$-phenyl | 24 | NA | NA | NA |
| r | naphthyl | 14 | NA | NA | NA |
| s | benzodioxole | 15 | 14 | NA | NA |
| t | 2,3,4-triOCH$_3$-phenyl | 15 | NA | NA | NA |
| Control | Chloramphenicol | 25 | 32 | 8 | 28 |
| Control | DMSO | NA | NA | NA | NA |

In one embodiment, the compounds may be synthesized by the following:

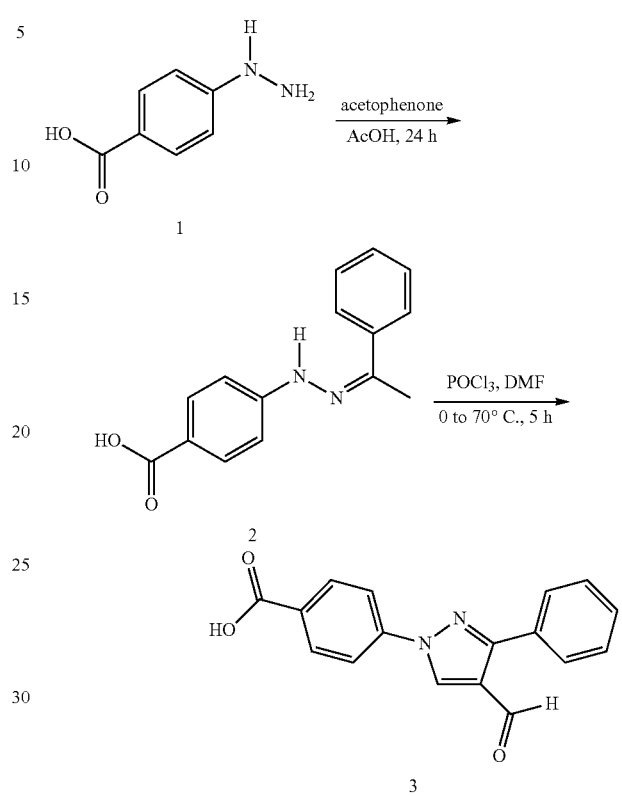

The compounds identified above can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like.

A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

REFERENCES

1. Centers for Disease Control and Prevention About Antimicrobial Resistance. http://www.cdc.gov/drugresistance/about.html (accessed Dec. 6, 2015).
2. WHO Antimicrobial resistance. http://www.who.int/mediacentre/factsheets/fs194/en/(accessed Dec. 12, 2015).
3. Fischbach, M. A.; Walsh, C. T., Antibiotics for emerging pathogens. *Science* 2009, 325 (5944), 1089-93.
4. Mohammad, H.; Mayhoub, A. S.; Ghafoor, A.; Soofi, M.; Alajlouni, R. A.; Cushman, M.; Seleem, M. N., Discovery and characterization of potent thiazoles versus methicillin- and vancomycin-resistant *Staphylococcus aureus*. *J Med Chem* 2014, 57 (4), 1609-15.
5. Disease, N. I. o. A. a. I. Methicillin-Resistant *Staphylococcus aureus* (MRSA). http://www.niaid.nih.gov/topics/ antimicrobialresistance/examples/mrsa/pages/default-.aspx (accessed Oct. 30, 2015).
6. Barreiro, E. J., Privileged Scaffolds in Medicinal Chemistry: Design, Synthesis, Evaluation. Royal Society of Chemisty: 2015; pp 115-131
7. Keri, R. S.; Chand, K.; Ramakrishnappa, T.; Nagaraja, B. M., Recent progress on pyrazole scaffold-based antimycobacterial agents. *Arch Pharm (Weinheim)* 2015, 348 (5), 299-314.
8. Kucukguzel, S. G.; Senkardes, S., Recent advances in bioactive pyrazoles. *Eur J Med Chem* 2015, 97, 786-815.
9. Baraldi, P. G.; Tabrizi, M. A.; Preti, D.; Bovero, A.; Fruttarolo, F.; Romagnoli, R.; Zaid, N. A.; Moorman, A. R.; Varani, K.; Borea, P. A., New 2-arylpyrazolo[4,3-c]quinoline derivatives as potent and selective human A(3) adenosine receptor antagonists. *J Med Chem* 2005, 48 (15), 5001-5008.
10. (a) Rathelot, P.; Azas, N.; El-Kashef, H.; Delmas, F.; Di Giorgio, C.; Timon-David, P.; Maldonado, J.; Vanelle, P., 1,3-Diphenylpyrazoles: synthesis and antiparasitic activities of azomethine derivatives. *Eur J Med Chem* 2002, 37 (8), 671-9; (b) Ragab, F. A.; Abdel Gawad, N. M.; Georgey, H. H.; Said, M. F., Synthesis of novel 1,3,4-trisubstituted pyrazoles as anti-inflammatory and analgesic agents. *Eur J Med Chem* 2013, 63, 645-54.
11. *Methods for Dilution Antimicrobial Susceptibility Tests for Bacteria That Grow Aerobically; Approved Standard—Ninth Edition* Clinical and Laboratory Standards Institute: Wayne, Pa., 2012; p CLSI document M07-A9.
12. (a) Drummond, A. J.; Waigh, R. D., The development of microbiological methods for phytochemical screening. *Recent Res. Dev. Phytochem.* 2000, 4, 143-152; (b) Sarker, S. D.; Nahar, L.; Kumarasamy, Y., Microtitre plate-based antibacterial assay incorporating resazurin as an indicator of cell growth, and its application in the in vitro antibacterial screening of phytochemicals. *Methods (Oxford, U. K.)* 2007, 42 (4), 321-324.

From the foregoing, it will be seen that the present invention is one well adapted to obtain all the ends and objects herein set forth, together with other advantages which are inherent to the structure.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A composition comprising a compound having a formula

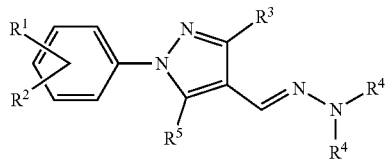

or a salt thereof;

wherein $R^1$ is selected from fluorine, a branched or unbranched, substituted or unsubstituted $C_2$-C12 alkyl, methoxy, nitrogen dioxide, carboxyl, sulfonamide, tetrazole, triazole, or trifluoromethyl;

wherein $R^2$ is selected from hydrogen, fluorine, chlorine, bromine, a branched or unbranched, substituted or unsubstituted $C_1$-$C_{12}$ alkyl, methoxy, nitrogen dioxide, carboxyl, or trifluoromethyl;

wherein $R^3$ is selected from hydrogen, a branched or unbranched, substituted or unsubstituted $C_1$-$C_6$ alkyl, phenyl, aryl, trifluoromethylphenyl, halophenyl, coumarinyl, hydroxycoumarinyl, naphthalinyl, or methoxy naphthalinyl;

wherein $R^4$ is selected from a branched or unbranched, substituted or unsubstituted $C_1$-$C_6$ alkyl, phenyl, aryl, trifluoromethylphenyl, halophenyl, coumarinyl, hydroxycoumarinyl, naphthalinyl, or methoxy naphthalinyl; and wherein $R^5$ is selected from hydrogen or methyl.

2. A composition comprising:
a compound as described in claim 1 or a pharmaceutically acceptable salt thereof; and a pharmaceutically acceptable diluent or carrier.

3. A composition comprising a compound having a formula

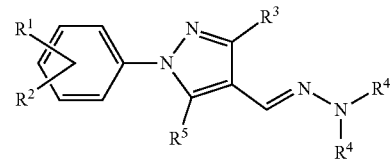

or a salt thereof;

wherein $R^1$ is selected from fluorine, a branched or unbranched, substituted or unsubstituted $C_2$-$C_{12}$ alkyl, methoxy, nitrogen dioxide, carboxyl, sulfonamide, tetrazole, triazole, or trifluoromethyl;

wherein $R^2$ is selected from hydrogen, fluorine, chlorine, bromine, a branched or unbranched, substituted or unsubstituted $C_1$-$C_{12}$ alkyl, methoxy, nitrogen dioxide, carboxyl, or trifluoromethyl;

wherein $R^3$ is selected from a branched or unbranched, substituted or unsubstituted $C_2$-$C_6$ alkyl, phenyl, aryl, trifluoromethylphenyl, halophenyl, coumarinyl, hydroxycoumarinyl, naphthalinyl, or methoxy naphthalinyl;

wherein $R^4$ is selected from a branched or unbranched, substituted or unsubstituted $C_1$-$C_6$ alkyl, phenyl, aryl, trifluoromethylphenyl, halophenyl, coumarinyl, hydroxycoumarinyl, naphthalinyl, or methoxy naphthalinyl; and wherein $R^5$ is selected from hydrogen or methyl.

4. A composition comprising:
a compound as described in claim 3 or a pharmaceutically acceptable salt thereof; and
a pharmaceutically acceptable diluent or carrier.

* * * * *